United States Patent
Sarwal et al.

(10) Patent No.: US 12,351,874 B2
(45) Date of Patent: Jul. 8, 2025

(54) ASSESSING TRANSPLANT REJECTION STATUS BY ANALYSIS OF T-CELL RECEPTOR SUBUNIT REPERTOIRE DIVERSITY

(71) Applicant: THE REGENTS OF THE UNIVERSITY OF CALIFORNIA, Oakland, CA (US)

(72) Inventors: Minnie Sarwal, Portola Valley, CA (US); Marina Sirota, Belmont, CA (US); Silvia Pineda San Juan, San Francisco, CA (US)

(73) Assignee: The Regents of The University of California, Oakland, CA (US)

( * ) Notice: Subject to any disclaimer, the term of this patent is extended or adjusted under 35 U.S.C. 154(b) by 1336 days.

(21) Appl. No.: 16/980,369

(22) PCT Filed: Mar. 12, 2019

(86) PCT No.: PCT/US2019/021918
§ 371 (c)(1),
(2) Date: Sep. 11, 2020

(87) PCT Pub. No.: WO2019/178143
PCT Pub. Date: Sep. 19, 2019

(65) Prior Publication Data
US 2021/0238681 A1 Aug. 5, 2021

Related U.S. Application Data

(60) Provisional application No. 62/641,992, filed on Mar. 12, 2018.

(51) Int. Cl.
*C12Q 1/6883* (2018.01)

(52) U.S. Cl.
CPC ..... *C12Q 1/6883* (2013.01); *C12Q 2600/158* (2013.01)

(58) Field of Classification Search
CPC ............ C12Q 1/6883; C12Q 2600/158; G01N 2333/7051; G01N 2800/245; G01N 33/6893
See application file for complete search history.

(56) References Cited

U.S. PATENT DOCUMENTS

| | | |
|---|---|---|
| 2010/0022627 A1 | 1/2010 | Scherer |
| 2014/0336056 A1 | 11/2014 | Erlich et al. |
| 2015/0252109 A1 | 9/2015 | Getts et al. |
| 2015/0301022 A1 | 10/2015 | Hermine et al. |
| 2016/0060701 A1 | 3/2016 | Schwartz et al. |

FOREIGN PATENT DOCUMENTS

| | | | |
|---|---|---|---|
| CN | 102221607 A | 10/2011 | |
| KR | 10-2016-0142390 A | 12/2016 | |
| WO | 2014/074501 A1 | 5/2014 | |
| WO | WO-2014189635 A1 * | 11/2014 | ........... A61K 31/519 |

OTHER PUBLICATIONS

Morris et al. "Tracking donor-reactive T cells: Evidence for clonal deletion in tolerant kidney transplant patients" Sci. Transl. Med. (2015) 7: 1-11 (Year: 2015).*
Gong, Qiang, et al. "Assessment of T-cell receptor repertoire and clonal expansion in peripheral T-cell lymphoma using RNA-seq data." Scientific reports 7.1 (2017): 11301. (Year: 2017).*
Lamarche, Caroline, et al. "Efficacy of acute cellular rejection treatment according to Banff score in kidney transplant recipients: a systematic review." Transplantation direct 2.12 (2016): e115. (Year: 2016).*
Suaywan, Kongsak, Veerapatr Nimkietkajorn, and Lersan Luesutthiviboon. "Intensive plasmapheresis and intravenous immunoglobulin for treatment of antibody-mediated rejection after kidney transplant." Exp Clin Transplant 4 (2014): 328-33. (Year: 2014).*
Alachkar, Houda, et al. "Quantitative characterization of T-cell repertoire and biomarkers in kidney transplant rejection." BMC nephrology 17 (2016): 1-9 (Year: 2016).*
Miqueu, Patrick, et al. "Analysis of the peripheral T-cell repertoire in kidney transplant patients." European journal of immunology 40.11 (2010): 3280-3290 (Year: 2010).*
Abdelhakim et al., "Role of alpha-beta T Cell Depletion in Prevention of Graft versus Host Disease," Biomedicines, 5(4), Jun. 26, 2017, p. 35.
European Patent Application No. 19766934.4, "Supplementary European Search Report," Nov. 4, 2021, 15 pages.
Galimberti et al., "Different gamma/delta T clones sustain GVM and GVH effects in multiple myeloma patients after non-myeloablative transplantation," Leukemia Research, 30(5), May 1, 2006, pp. 529-535.
Kirk et al., "Characterization of T cells expressing the gamma/delta antigen receptor in human renal allografts," Human Immunology, 36(1), Jan. 1, 1993, pp. 11-19.

(Continued)

*Primary Examiner* — Jennifer Dunston
*Assistant Examiner* — John Charles McKillop
(74) *Attorney, Agent, or Firm* — Kilpatrick Townsend & Stockton LLP

(57) ABSTRACT

Disclosed are novel methods of assessing transplant rejection status in a transplant recipient, such as a kidney transplant recipient. The diagnostic method identifies stable subjects, subjects undergoing cell mediated rejection processes, and subjects undergoing antibody mediated rejection processes using measurement of TCR subunit repertoire diversity. The proportion of unique TCR alpha and beta subunit sequences to total unique TCR subunit sequences (total sequences for alpha, beta, delta, and gamma subunits) provides a diagnostic measure that can identify stable subjects, subjects undergoing cell mediated rejection processes, and subjects undergoing antibody mediated rejection processes. Methods of treatment include administration of a suitable treatment if antibody mediated rejection or cell mediated rejection is detected.

6 Claims, 5 Drawing Sheets

(56) References Cited

OTHER PUBLICATIONS

Li et al., "Analyses of peripheral blood mononuclear cells in operational tolerance after pediatric living donor liver transplantation," American Journal of Transplantation, 4(1), Jan. 1, 2004, pp. 2118-2125.

Liu et al., "Longitudinal Analysis of T-Cell Receptor Variable Beta Chain Repertoire in Patients with Acute Graft-versus-Host Disease after Allogeneic Stem Cell Transplantation," Biology of Blood and Marrow Transplantation, 12(3), Mar. 1, 2006, pp. 335-345.

Oaks et al., "T-Cell Receptor alpha and beta Chain Gene Expression in Cells Infiltrating Human Cardiac Allografts," American Journal of Medical Sciences, 309(1), Jan. 1, 1995, pp. 26-34.

* cited by examiner

Total Reads
p-value (clinSTA to clinCMR) = 0.1488
p-value (clinSTA to clinAMR) = 0.572
p-value (clinCMR to clinAMR) = 0.0472

Total Clones
p-value (CMR) = 0.0176
p-value (AMR) = 0.0559

TRA/TRB to TRD/TRG Ratio
p-value (clinSTA to clinCMR) = 0.012855
p-value (clinSTA to clinAMR) = 0.000104
p-value (clinCMR to clinAMR) = 0.0725

ASSESSING TRANSPLANT REJECTION STATUS BY ANALYSIS OF T-CELL RECEPTOR SUBUNIT REPERTOIRE DIVERSITY

CROSS-REFERENCE TO RELATED APPLICATIONS

This application is a 35 USC § 371 National Stage application of PCT International Application Number PCT/US2019/021918, entitled "Assessing Transplant Rejection Status by Analysis of T-Cell Receptor Subunit Repertoire Diversity," filed Mar. 12, 2019, which claims the benefit of priority to U.S. Provisional Application Ser. No. 62/641,992, entitled "Kidney Transplant Rejection And T-Cell Receptor Subunit Repertoire," filed Mar. 12, 2018, the contents which are hereby incorporated by reference.

STATEMENT REGARDING FEDERALLY SPONSORED RESEARCH OR DEVELOPMENT

This invention was made with government support under grant number U19 AI128913 awarded by the National Institutes of Health. The government has certain rights in the invention.

BACKGROUND OF THE INVENTION

Transplant rejection is a serious problem affecting a significant portion of kidney transplant recipients. There are two major forms of kidney rejection: antibody mediated rejection (AMR), mediated by antibodies, and cell-mediated rejection (CMR), mediated by T-cells. Importantly, the two forms of rejection have different prognoses and are treated by different methods, as known in the art. Accordingly, it would be advantageous to be able to identify when rejection is occurring in a kidney transplant recipient and to be able to accurately diagnose which form of rejection the subject is suffering from. It would further be of advantage to identify patients at risk of or undergoing AMR or CMR by means of an easily-obtained sample, as opposed to an invasive graft biopsy Due to the recombination process a high variability of BCR and TCR is possible, enabling T cell activation by diverse antigens. This recombination involves three different gene segment types: V (variable), D (diversity) and J (joining) segments, resembling recombination in immunoglobulins. Additional diversity is generated at the junction of the segments during the recombination process. The TCR complex comprises multiple subunits, including heterodimers of the alpha subunit and beta subunit and heterodimers of the delta and gamma subunits. The majority of heterodimers, and the majority of clonal diversity exists among the alpha and beta subunits, and the proportion of heterodimers is generally known to change during disease progression. As disclosed herein, the inventors of the present disclosure have determined that certain measures of TCR subunit diversity provide a diagnostic signature indicative of graft rejection status.

SUMMARY OF THE INVENTION

The inventors of the present disclosure have developed novel means of assessing whether transplant recipients are stable (not undergoing rejection processes) from subjects that are undergoing some form of immune mediated rejection. The methods can also be used to determine whether AMR or CMR processes are active in the transplant recipient. The methods are accomplished by analysis of the diversity of certain T cell receptor subunits. Advantageously, these T cell receptor subunit diversity measures can be assessed in peripheral blood samples, which enables facile and non-invasive assessments of kidney rejection status.

The invention is based on the discovery that a ratio comprising the abundance of alpha and beta T cell receptor subunit clonotypes to the total number of alpha, beta, gamma and delta T cell receptor subunit clonotypes, is highly indicative of kidney transplant rejection status. The predictive ratio can be expressed as:

$$(N\alpha+N\beta):(N\alpha+N\beta+N\delta+N\gamma)$$

wherein $N\alpha$ is the number of unique alpha subunit sequences, $N\beta$ is the number of unique beta subunit sequences, $N\delta$ is the number of unique delta subunit sequences, $N\gamma$ is the number of unique gamma subunit sequences. Thus, the diagnostic ratio represents the proportion of total subunit diversity (total unique clonotypes) that is represented by alpha and beta subunit clonotype diversity.

In a first aspect, the scope of the invention encompasses novel methods of diagnosing ongoing transplant rejection processes in a subject by the measured diversity of TCR subunits. The methods of the invention enable determination of rejection status, wherein no rejection, AMR rejection, and CMR rejection status can be determined. The methods of the invention may be applied to any transplant recipient, for example, kidney transplant recipients.

In a second aspect, the scope of the invention encompasses novel methods of diagnosing ongoing transplant rejection processes in a subject by the measured expression levels of TCR subunits. For example, by comparison to subunit expression levels established for stable subjects, measurement of subunit expression levels may be used to determine rejection status, wherein no rejection, AMR rejection, and CMR rejection status can be assessed. The methods of the invention may be applied to any transplant recipient, for example, kidney transplant recipients In a third aspect, the scope of the invention encompasses novel methods of treating ongoing rejection in a transplant recipient, wherein transplant rejection status is determined, and upon such determination, a suitable treatment is administered to the subject.

BRIEF DESCRIPTION OF THE DRAWINGS

FIG. 1 depicts the subunit arrangements of T-Cell Receptor complexes.

FIG. 2 depicts the Sequence analysis workflow performed in Example 1 for samples from kidney recipients.

FIG. 3A is a boxplot depicting total reads and FIG. 3B is a boxplot depicting total clonotypes detected in sample pools of kidney recipients representing stable subjects, subjects undergoing AMR processes and subjects undergoing CMR processes.

FIG. 4 is a boxplot depicting the percentage of total reads for alpha and beta subunits in kidney recipients.

FIGS. 5A,5B, 5C, and 5D depict TCR subunit expression levels in samples from kidney recipients, including Stable (STA), AMR, and CMR rejection status. FIG. 5A depicts TCR-alpha subunit expression. FIG. 5A depicts TCR-alpha subunit expression. FIG. 5B depicts TCR-bets subunit expression. FIG. 5C depicts TCR-gamma subunit expression. FIG. 5D depicts TCR-delta subunit expression.

DETAILED DESCRIPTION OF THE INVENTION

Figure 1:
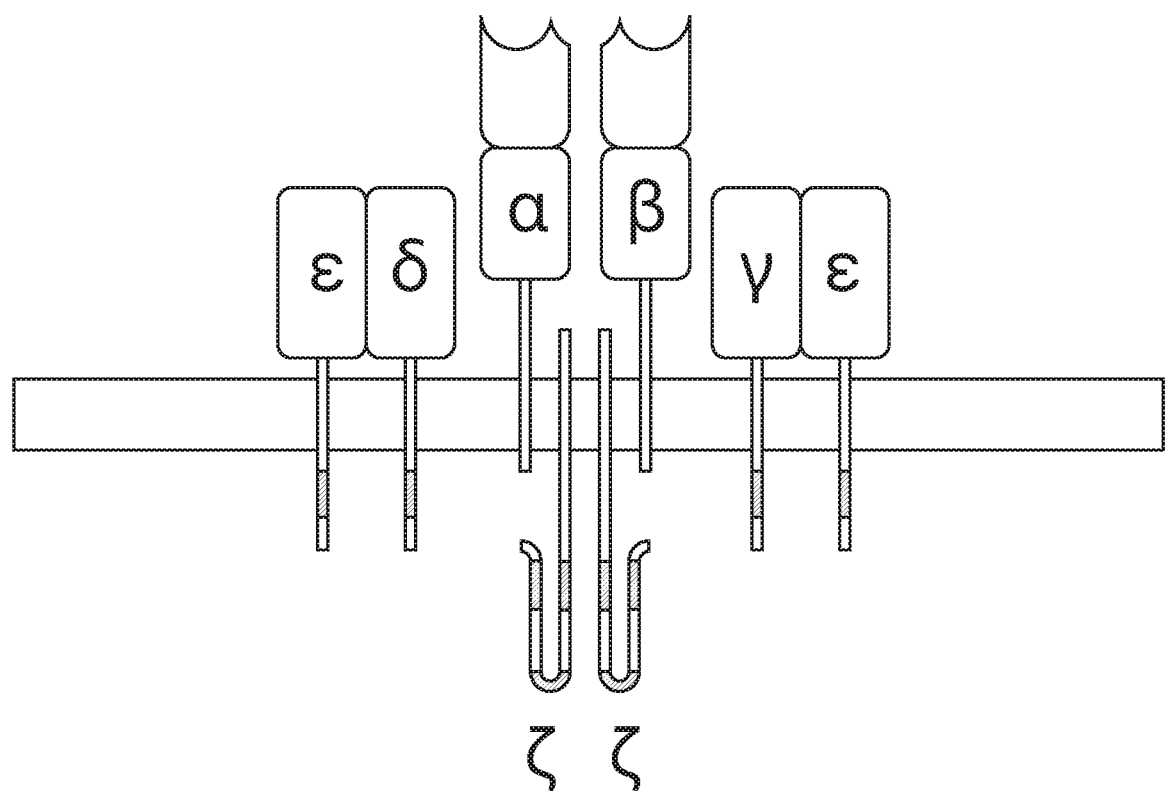
FIG. 1.

The various inventions disclosed herein are directed to assessing rejection status for a graft. The rejection status reflects whether there are substantial, ongoing rejection processes against the graft or whether the graft is stable. The rejection status also distinguishes between AMR and CMR rejection processes, which may be treated in different ways.

In a primary embodiment, the graft is a kidney graft. However, the general method of the invention may be applied in diagnosing and treating rejection processes in other graft types. The graft may comprise any selected graft type, for example, a type selected from the group consisting of an organ, tissue, cells, heart, lung, liver, skin, cornea, intestine, pancreas, limb, digit, bone, ligament, cartilage, and tendon. References to a graft, as used herein will encompass whole organs and portions thereof.

The transplant recipient subject may be a human, for example, the recipient may be a human patient that has received a transplant, e.g., a kidney transplant. In alternative embodiments, the subjects may comprise a non-human animal, for example a veterinary patient or test animal. For convenience, the description provided herein will be directed to human subjects. It is understood that one of skill in the art may apply the methods and compositions described herein to non-human animals by utilizing TCR repertoire analysis methods suitable for the selected non-human animal species.

The several embodiments of the invention are directed to assessing rejection status in a graft recipient. In some cases, the rejection status is "no rejection," which is the absence of substantial immune responses against the graft In some cases, the rejection status is the occurrence of antibody-mediated rejection, which is the occurrence of any antibody-mediated responses against the graft, antibody-mediated graft failure, for example, as mediated by donor-specific antibodies (DSA) which bind to antigens present in the graft, for example on the endothelium of the transplant, and/or any other measure of antibody-mediated injury and/or rejection.

In some cases, the rejection status is the occurrence of cell-mediated rejection, which is the occurrence of any T-cell-mediated responses against the graft, any injury to or failure of the graft mediated by T-cells activated against the transplanted tissue, the presence of activated T-cells against graft antigens, and/or any other measure of cell-mediated rejection.

The various embodiments of the invention encompass an assessment of T cell subunit repertoire diversity, specifically, the number of different clonotypes for each subunit. These numbers are utilized in a novel diagnostic ratio that is highly correlated with graft rejection status.

The general method of the invention encompasses a method of assessing transplant rejection status in transplant recipient subject, comprising the steps of
  obtaining a sample from the subject;
  assessing the subject's $(N\alpha+N\beta):(N\alpha+N\beta+N\delta+N\gamma)$ ratio by means of the sample; and
  determining the subject's transplant rejections status by comparing the observed $(N\alpha+N\beta):(N\alpha+N\beta+N\delta+N\gamma)$ ratio to statistically relevant ratios indicative of normal, CMR or AMR status.

The various methods disclosed herein are directed to the assessment of factors in a sample. The selected sample type may comprise any biological material containing T-lymphocytes. Peripheral blood is an especially convenient source that is readily withdrawn. Other sources of T-cells include, for example, serum, interstitial fluid, skin, oral swabs, saliva, urine, or tissue samples, e.g., tissue obtained by biopsy.

T-cells may be obtained from the sample by methodologies known in the art, for example by fluorescence activated cell sorting, magnetic cell sorting, leukapheresis, or density gradient centrifugation. Cells obtained by these methods may be further subdivided into functionally or developmentally distinct subsets, as known in the art.

The methods of the invention encompass the measurement TCR receptor diversity for each of the alpha, beta, delta, and gamma subunits, i.e., the number of unique clonotypes for each subunit type. In the practice of the invention, any suitable methodology that provides a measure of subunit diversity may be employed.

From the isolated T-cells, genetic material reflective of subunit sequence diversity may be obtained. Various methods are known in the art that utilize either genomic DNA or RNA. DNA provides better stability and may enable more accurate quantification of low-abundance TCR clonotypes. RNA, for example mRNA, is reflective of actual TCRs present in the cell and also provides information on the expression level of the genes selected for the analysis.

The selected genetic material may be analyzed by various methods known in the art for an assessment of clonotypes present for each subunit type. Practitioners may select various diversity assessment tools, including singe cell and bulk methods. Any TCR gene sequence reflective of subunit diversity may be selected, including analyses of the CDR3 region, for which numerous protocols are known. Analysis of CDR1 and CDR2 sequences may be performed as well. Practitioners may select from any number of established library preparation methods, for example multiplex PCR, targeted enrichment, and rapid amplification of 5' complementary DNA ends (5'RACE). Sequencing of the selected material may be performed using any sequencing platform known in the art, for example Illumina™, IonTorrent™ and Roche 454™ platforms. Exemplary methods include, for example, DNA barcoding, exhaustive sequencing, 5' RACE or other unbiased sequencing techniques, spectratyping, non-parametric abundance estimators, parametric estimators, the Chao1 estimator, Chao1-bc estimator, Chao2 estimator, abundance-based coverage estimator, incidence-based coverage estimators, f Poisson abundance models, and rarefaction curves.

In one embodiment, sequence diversity is assessed by RNA-Seq whole transcriptome shotgun sequencing, for example, as described by D. Bolotin, et al. MiXCR: software for comprehensive adaptive immunity profiling, Nature methods, 2015.

By the selected sequencing and analysis protocol, the number of clonotypes for each of the alpha, beta, delta and gamma subunits is determined. Surprisingly, the inventors of the present disclosure have discovered that rejection status is highly correlated with the ratio $$(N\alpha+N\beta):(N\alpha+N\beta+N\delta+N\gamma)$$

wherein $N\alpha$ is the number of unique alpha subunit sequences, $N\beta$ is the number of unique beta subunit sequences, $N\delta$ is the number of unique delta subunit sequences, $N\gamma$ is the number of unique gamma subunit sequences; and wherein the ratio may be expressed as a percentage value.

Specifically, the inventors of the present disclosure have determined that a relatively low value for the diagnostic ratio is indicative of stable status, i.e., no substantial rejection processes; an intermediate value of the diagnostic ratio is indicative of ongoing CMR processes, and a relatively high value of the diagnostic ratio is indicative of ongoing AMR processes.

Utilizing this teaching, one of skill in the art can determine ratios associated with stable, CMR, and AMR rejection status for any for transplant type and population of interest. This is achieved for a selected transplant type, selected recipient population, and selected diversity assessment methodology by analyzing samples from pools of appropriately matched subjects (e.g. subjects receiving the same graft type, subjects having similar health and demographic factors, etc.) representing stable, AMR, CMR, and optionally, mixed AMR/CMR rejection status. For example, thresholds may be established by a use of a historical prospective study, a retrospective cohort study, or like analysis.

From these measurements, statistically validated threshold values may be calculated for each rejection status category. The statistically validated threshold value is a value or range of values of the diagnostic ratio that can be used to classify subjects according to rejection status. The (Nα+Nβ):(Nα+Nβ+Nδ+Nγ) statistics for the population of interest can be used to develop a classifier or other predictive model. Subsequently, the resulting classifier can be used to assess rejection status of any individual in the population by measuring (Nα+Nβ):(Nα+Nβ+Nδ+Nγ) in samples from the individual.

Such threshold or cut-off may be selected by methods generally known in the art to provide for a chosen sensitivity and/or specificity of the rejection status assessment, e.g., sensitivity and/or specificity of at least 50%, or at least 60%, or at least 70%, or at least 80%, or at least 85%, or at least 90%, or at least 95%. The designation of rejection status may be selected at any selected level of confidence, for example, a probability, for example, a probability of a particular rejection status greater than 5%, greater than 10%, greater than 20%, greater than 30%, greater than 40%, greater than 50%, greater than 60%, greater than 70%, greater than 80%, or greater than 90% probability. In one implementation, the rejection status comprises a probability score, i.e. a measure of the likelihood that the subject will be of a particular rejection status.

The threshold values of the invention may be established using any statistical methods known in the art and suitable for associating the diagnostic ratio to rejection status. Exemplary methods of generating thresholds include logistic regression, linear regression methods, machine learning classifiers such as random forest, support vector machines, and deep learning and neural network approaches.

In one implementation, the rejection status of kidney transplant recipients may be assessed. In one implementation, stable kidney rejection status is established for subjects having a diagnostic ratio value within the 3% standard deviation of 91%. In one implementation, CMR rejection status is established for subjects having a diagnostic ratio value within the 2% standard deviation of 95%. In one implementation, AMR rejection status is established for subjects having a diagnostic ratio value within the 2% standard deviation of 97%, or greater. Mixed AMR/CMR rejection status may optionally be established for subjects having a diagnostic ratio value between the selected thresholds for CMR and AMR status, for example, in the range of 94% to 99%. For example, in one implementation stable status is determined for subjects with a (Nα+Nβ):(Nα+Nβ+Nδ+Nγ) ratio of less than 94%; CMR rejection status is determined for subjects with (Nα+Nβ):(Nα+Nβ+Nδ+Nγ) ratio between 94% and 97%; and AMR rejection status is determined for subjects having a (Nα+Nβ):(Nα+Nβ+Nδ+Nγ) ratio of greater than 97%.

While the present disclosure is directed to a diagnostic ratio of (Nα+Nβ):(Nα+Nβ+Nδ+Nγ), it will be understood that the methods disclosed herein may be practiced using any diagnostically equivalent or highly correlated measure.

The diagnostic method may be performed as a routine post-transplant monitoring regimen that is performed at regular intervals. Early onset of rejection symptoms manifesting at the T cell receptor level can provide a means for early detection. In some implementations, the (Nα+Nβ):(Nδ+Nγ) ratio assessment can be applied as a diagnostic tool when for a subject that is displaying symptoms of potential rejection. For example, in the case of kidney rejection, symptoms indicating a need for diagnostic testing may include fever, fatigue, pain and tenderness in the area of the transplant, decreased urine output, or elevated biomarkers of graft injury, such as creatinine.

Assessment of Rejection Status by TCR Subunit Expression.

In another aspect, the expression of individual TCR subunit types can be used to assess rejection status. As depicted in FIGS. 5A, 5B, 5C, and 5D, individual subunit expression profiles are associated with rejection status. The general method encompasses a method of assessing transplant rejection status in transplant recipient subject, comprising the steps of obtaining a sample from the subject;
by the sample, assessing the subject's expression of one or more of TCR-alpha, TCR-beta, TCR-delta, and/or TCR-gamma subunits;
determining if the subject suffers from CMR, suffers from AMR, or is stable by and comparing the observed expression value of the one or more selected TCR subunits to values defining stable, AMR, or CMR rejection status for members of the selected population.

The measured expression level can be any measure of gene expression, for example, the abundance of transcripts coding for a selected TCR subunit type, the mean copy number for the selected TCR subunit type, the abundance of translated or functional TCR-subunits of the selected subunit type, or any other measure of expression known in the art.

In one implementation, assessment of rejection status may be determined by comparing expression levels of the one or more selected receptor subunits to threshold or range established for like, stable subjects. "Increased," and "decreased" expression of a selected subunit means with respect the of expression levels established for stable subjects of the same population. By this method, rejection status may be established by any of the following measures:

an increased expression of TCR alpha subunits is indicative of AMR;
a reduced expression of TCR-beta subunits is indicative of AMR;
a reduced expression of TCR gamma subunits is indicative of AMR;
a reduced expression of TCR-delta subunits is indicative of AMR.
a decreased expression of TCR-beta subunits is indicative of CMR;
a decreased expression of TCR-delta subunits is indicative of CMR;
a decreased expression of TCR-gamma subunits is indicative of CMR;
CMR is indicated when TCR-alpha expression is normal (at same level for stable subjects) but elevated and there is decreased TCR-beta, TCR-delta, and/or TCR-gamma expression;

AMR is indicated when TCR-alpha expression is elevated and there is decreased TCR-beta, TCR-delta, and/or TCR-gamma expression;

CMR is indicated when TCR-delta expression is intermediate between levels seen for stable and AMR subjects; and stable rejection status is indicated when expression of TCR-beta, TCR-delta, or TCR gamma is not increased or decreased relative to expression levels established for stable subjects.

Methods of Treatment. In another aspect, the scope of the invention encompasses a method of treating a subject potentially suffering from a rejection processes, comprising, obtaining a sample from the subject that is a member of a selected population;

by the sample, assessing the subject's (Nα+Nβ):(Nα+Nβ+Nδ+Nγ) ratio and;

determining if the subject suffers from CMR, suffers from AMR, or is stable by comparing the observed (Nα+Nβ):(Nα+Nβ+Nδ+Nγ) to ratios defining stable, CMR, or AMR rejection status for members of the selected population; and administering a treatment appropriate for CMR if the subject is determined to have CMR rejection; administering a treatment appropriate for AMR if the subject is determined to have AMR; and administering no treatment if the subject is determined to be stable.

In one embodiment, the subject is a kidney recipient.

In another implementation, the scope of the invention encompasses a method of treating a subject potentially suffering from a rejection processes, comprising, obtaining a sample from the subject that is a member of a selected population;

by the sample, assessing the subject's expression of one or more TCR subunits;

determining if the subject suffers from CMR, suffers from AMR, or is stable by and comparing the observed expression value of the one or more selected TCR subunits to values defining stable, AMR, or CMR rejection status for members of the selected population; and administering a treatment appropriate for CMR if the subject is determined to have CMR rejection; administering a treatment appropriate for AMR if the subject is determined to have AMR; and administering no treatment if the subject is determined to be stable.

In one embodiment, the expression of one or more TCR subunits comprises the expression of TCR-alpha, TCR-beta, TCR-delta, and TCR-gamma. In one embodiment, the subject is a kidney transplant recipient. In one embodiment, the values defining stable rejection status are the values depicted in FIGS. 5A, 5B, 5C, and 5D.

If CMR rejection status is detected, treatments appropriate for mitigating CMR may be administered, for example, the administration of corticosteroids and T cell-depleting agents. If AMR rejection status is detected, treatments appropriate for treating AMR may be applied, for example, plasmapheresis, administration of intravenous immune globulin, or B cell depletion therapy.

In an alternative embodiment, the method of treatment may be used to distinguish normal subjects from subjects having any form of rejection, and administering a treatment appropriate to all forms of transplant rejection relevant to the subject if the subject is determined to be undergoing rejection processes.

EXAMPLES

Figure 2:
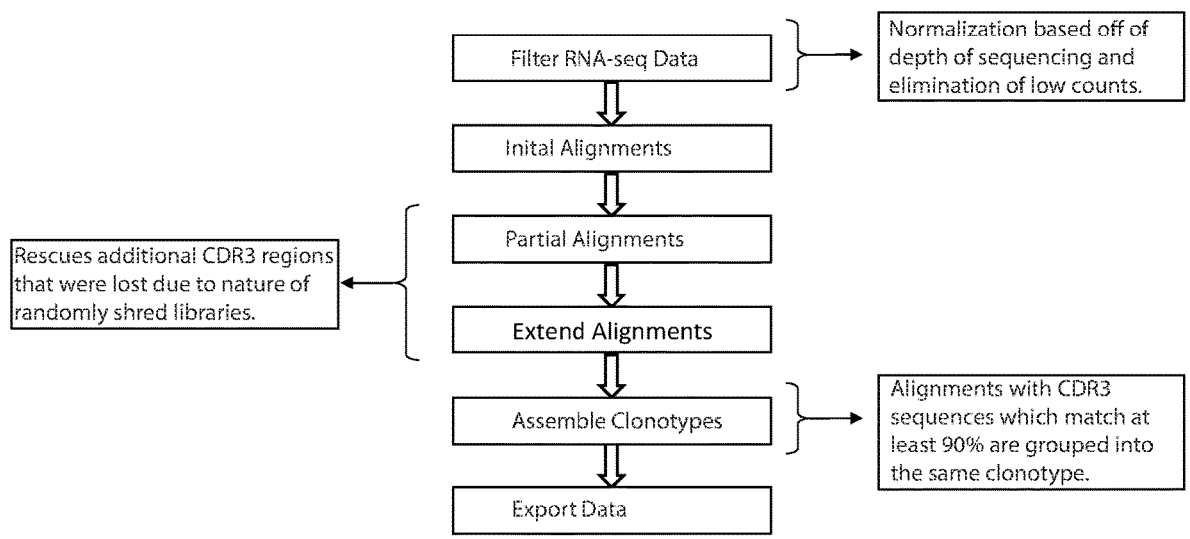
FIG. 2.
Figure 3A:
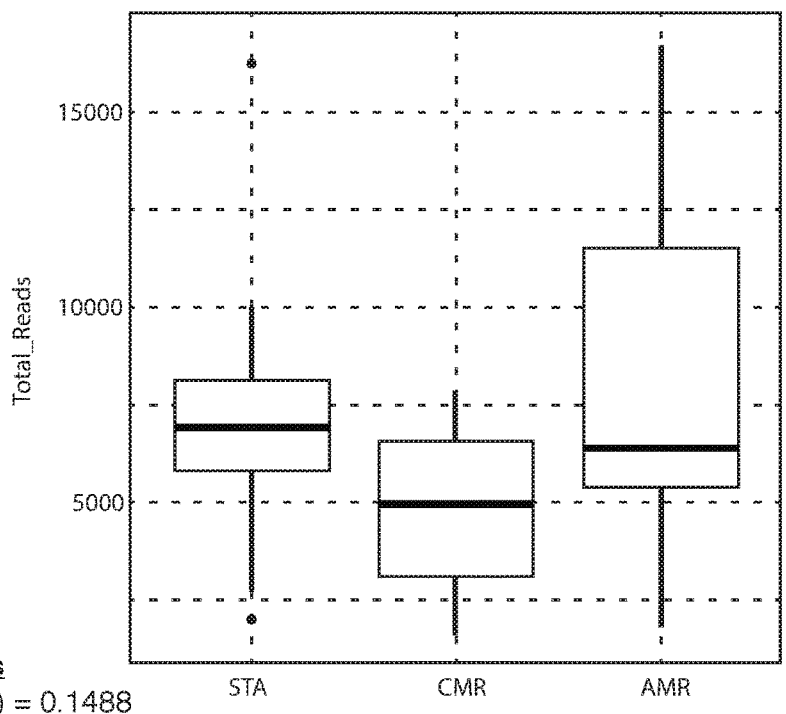
FIGS. 3A and 3B.
Figure 3B:
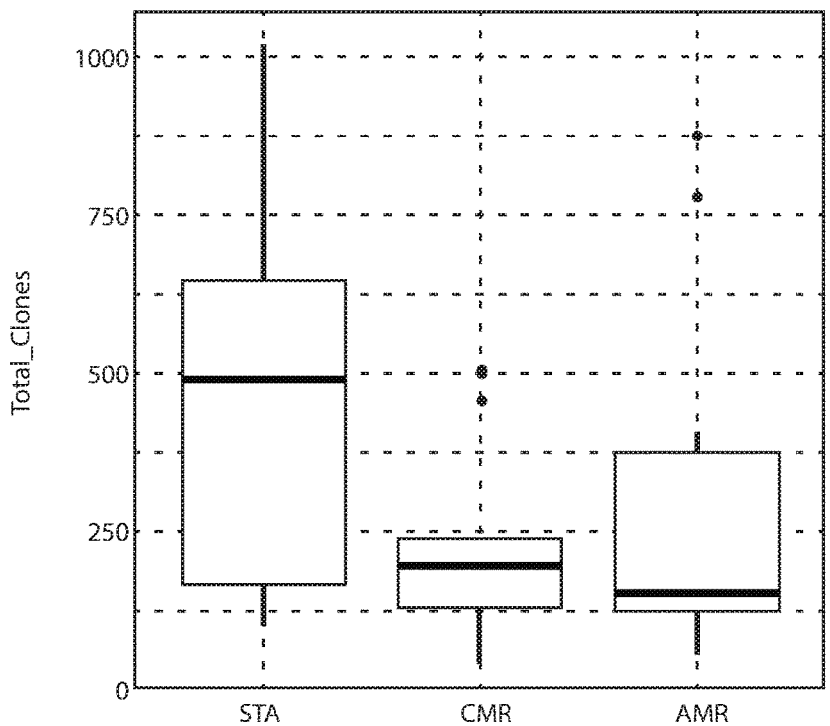
Figure 4:
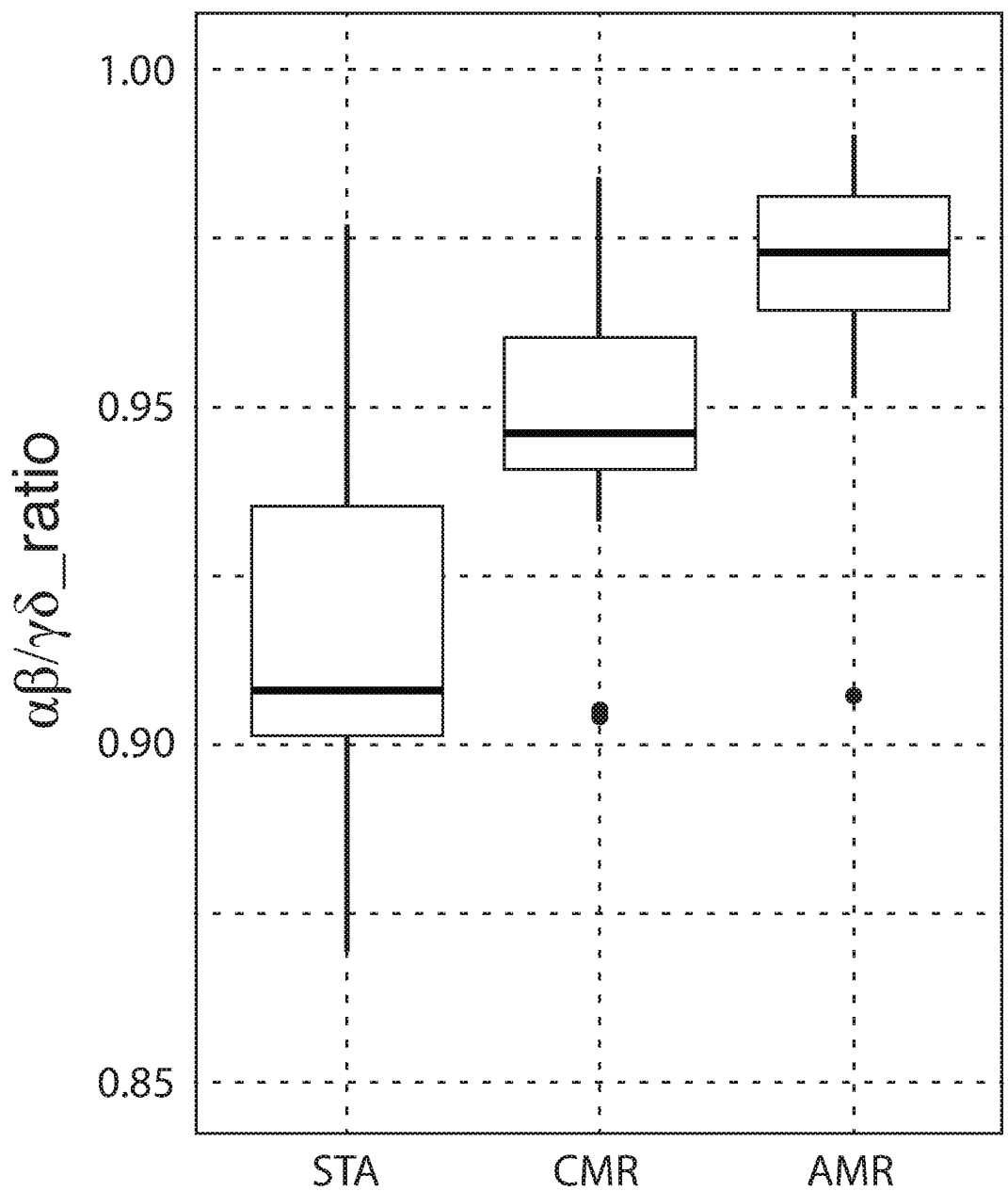
FIG. 4.
Figure 5A:
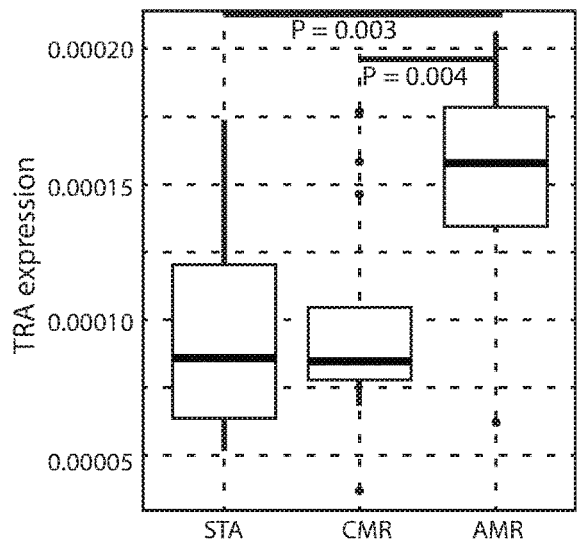
FIGS. 5A, 5B, 5C, and 5D.
Figure 5B:
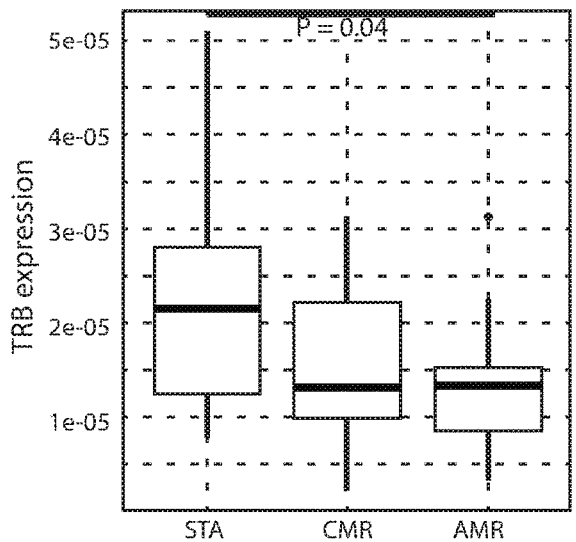
Figure 5C:
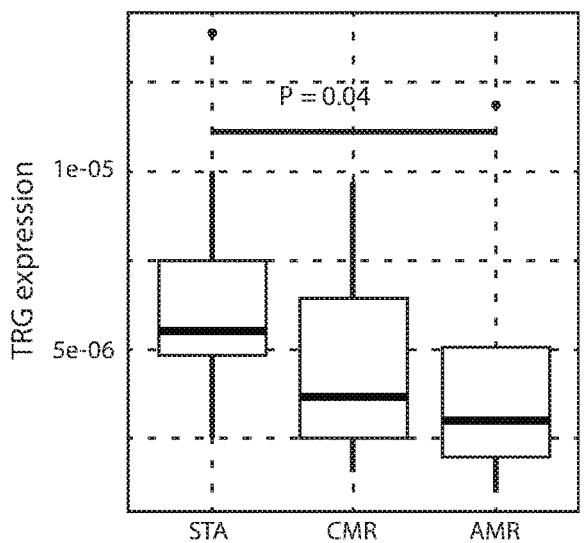
Figure 5D:
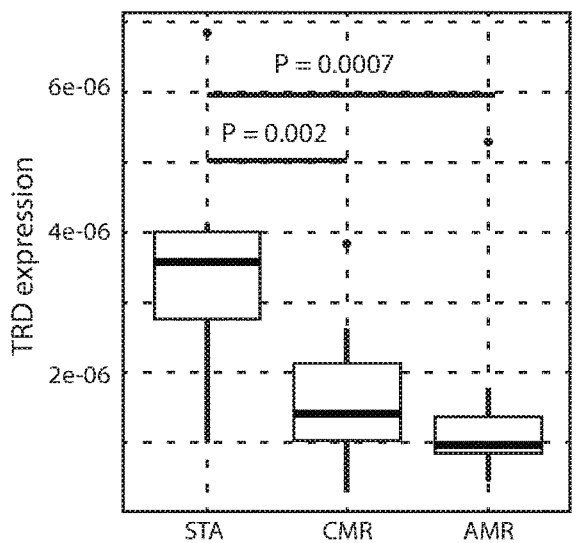

Example 1. Development of the Diagnostic Ratio in Kidney Transplant subjects. Peripheral blood was collected from 37 human kidney transplant recipients. Twelve of the samples were obtained from stable subjects having no symptoms of rejection. Thirteen samples were obtained from subjects determined to be undergoing CMR processes, with samples obtained prior to any additional immunosuppressive intervention. Twelve samples were obtained from subjects determined to be undergoing AMR processes, with samples obtained prior to any additional immunosuppressive intervention. Sequence diversity for TCR alpha, beta, delta, and gamma subunits CDR3 sequences was determined using RNA-Seq methodology performed with MixCR software (MiLaboratory LLC) workflow, as depicted in FIG. 2. For stable subjects, an average of 7,234 reads and 497 total clones was observed (143 alpha clonotypes, 164 beta clonotypes, 8 delta clonotypes, and 68 gamma clonotypes). For CRM subjects, an average of 5,059 reads and 237 clonotypes was observed (63 alpha clonotypes, 81 beta clonotypes, 2 delta clonotypes, and 34 gamma clonotypes). For AMR subjects, an average of 8,090 reads and 286 total clones was observed (75 alpha clonotypes, 79 beta clonotypes, 3 delta clonotypes, and 26 gamma clonotypes).

Average values of the (Nα+Nβ):(Nα+Nβ+Nδ+Nγ) diagnostic ratios were 91% for stable subjects, 95% for CMR subjects, and 97% for AMR subjects.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of treating transplant rejection in a transplant recipient subject, comprising performing an assessment of the rejection status of the subject to determine if the subject is undergoing Cell Medicated Cell-Mediated Rejection (CMR), or undergoing Antibody Medicated Antibody-Mediated Rejection (AMR);

wherein the assessment of rejection status in the transplant recipient subject comprises the steps of obtaining a sample from the subject;

determining an observed assessing the subject's (Nα+Nβ):(Nα+Nβ+Nδ+Nγ) ratio by means of the sample, wherein Nα is the number of unique T cell receptor (TCR) alpha subunit sequences, Nβ is the number of unique TCR beta subunit sequences, Nδ is the number of unique TCR delta subunit sequences, Nγ is the number of unique TCR gamma subunit sequences; and determining the subject's transplant rejection status in the subject is undergoing CMR or AMR by comparing when the observed (Nα+Nβ):(Nα+Nβ+Nδ+Nγ) ratio to threshold values indicative of CMR or AMR rejection status, wherein the threshold value indicative of CMR rejection status is between 94% and 97%, or determining the subject is undergoing AMR when wherein the threshold value indicative of AMR rejection status the observed (Nα+Nβ):(Nα+Nβ+Nδ+Nγ) ratio is greater than 97%;

and administering a treatment appropriate for CMR to the subject undergoing CMR, wherein the treatment appropriate for CMR comprises administration of corticosteroids and/or T cell-depleting agents; or administering a treatment appropriate for AMR to the subject undergoing AMR, wherein the treatment appropriate for AMR is selected from the group consisting of plasmapheresis, administration of intravenous immune globulin, and B cell depletion therapy.

2. The method of claim 1, wherein the transplant recipient is a kidney transplant recipient.

3. The method of claim 1, wherein the transplant recipient is the recipient of a graft selected from the group consisting of organ, tissue, cells, heart, lung, liver, skin, cornea, intestine, pancreas, limb, digit, bone, ligament, cartilage, and tendon.

4. The method of claim 1, wherein $N\alpha$, $N\beta$, $N\delta$, and $N\gamma$ sequence diversity is assessed by RNA-Seq.

5. The method of claim 1, wherein the subject is determined to be undergoing CMR and the administering comprises administering the treatment appropriate for CMR comprising administration of corticosteroids and/or T cell-depleting agents.

6. The method of claim 1, wherein the subject is determined to be undergoing AMR and the administering comprises administering the treatment appropriate for AMR selected from the group consisting of plasmapheresis, administration of intravenous immune globulin, and B cell depletion therapy.

* * * * *